US010625027B2

(12) United States Patent
Sjöstedt (10) Patent No.: US 10,625,027 B2
(45) Date of Patent: Apr. 21, 2020

(54) USING A MOBILE PHONE FOR MONITORING A MEDICAL DEVICE (71) Applicant: Brighter AB (publ), Kista (SE)

(72) Inventor: Truls Sjöstedt, Täby (SE)

(73) Assignee: Brighter AB (publ), Kista (SE)

( * ) Notice: Subject to any disclaimer, the term of this patent is extended or adjusted under 35 U.S.C. 154(b) by 0 days.

(21) Appl. No.: 16/311,567

(22) PCT Filed: Jun. 9, 2017

(86) PCT No.: PCT/EP2017/064165
§ 371 (c)(1),
(2) Date: Dec. 19, 2018

(87) PCT Pub. No.: WO2018/007100
PCT Pub. Date: Jan. 11, 2018

(65) Prior Publication Data
US 2019/0240414 A1 Aug. 8, 2019

(30) Foreign Application Priority Data
Jul. 7, 2016 (SE) ...................................... 1651008

(51) Int. Cl.
*H04W 24/00* (2009.01)
*A61M 5/315* (2006.01)
*G16H 40/63* (2018.01)
*G16H 40/40* (2018.01)
(Continued)

(52) U.S. Cl.
CPC ...... *A61M 5/3158* (2013.01); *A61M 5/31548* (2013.01); *G06F 1/163* (2013.01);
(Continued)

(58) Field of Classification Search
CPC ............ A61M 5/3158; A61M 5/31548; A61M 2205/3553; A61M 2205/3584;
(Continued)

(56) References Cited

U.S. PATENT DOCUMENTS 7,580,755 B1 * 8/2009 Schwartz ........... A61N 1/37282
128/903
9,087,358 B1 7/2015 Giorgalli
(Continued)

OTHER PUBLICATIONS

Data Fusion, Wikipedia, Feb. 28, 2016, 6 pages.
(Continued)

*Primary Examiner* — Danh C Le
(74) *Attorney, Agent, or Firm* — Tucker Ellis LLP (57) ABSTRACT There is provided a method involving a portable medical device (1), being carried by a user and a mobile phone (2) carried by the same user, the method comprising the steps of a) the mobile phone (2) at a time point (first time point) determining a geographical position of the mobile phone (2), and providing the geographical position and the first time point to a server (4) via a data connection, or the mobile phone (2) having its position determined by the cell network (3), and the cell network (3) providing the position and the first time point to the server (4), then b) the server (4) using the position and the time point to retrieve position-specific data for the time point, then c) the server (4) using a the data from step b. to determine whether the medical device should be serviced or replaced. There is also provided a system, a server and a mobile phone.

11 Claims, 9 Drawing Sheets (51) Int. Cl.
 H04W 4/029 (2018.01)
 G06F 1/16 (2006.01)
(52) U.S. Cl.
 CPC ............. *G16H 40/40* (2018.01); *G16H 40/63* (2018.01); *H04W 4/029* (2018.02); *A61M 2205/3553* (2013.01); *A61M 2205/3584* (2013.01); *A61M 2205/3592* (2013.01); *A61M 2205/50* (2013.01); *A61M 2205/52* (2013.01); *A61M 2205/702* (2013.01); *A61M 2205/8206* (2013.01)
(58) Field of Classification Search
 CPC ...... A61M 2205/3592; A61M 2205/50; G16H 40/40; G16H 40/63; H04W 4/029; G06F 1/163
 USPC ......... 455/456.1, 550.1, 456.5, 418
 See application file for complete search history.

(56) References Cited

U.S. PATENT DOCUMENTS

| | | | |
|---|---|---|---|
| 9,545,520 B2 * | 1/2017 | Matos | A61N 1/37264 |
| 2009/0150177 A1 * | 6/2009 | Buck | G06Q 50/22 705/2 |
| 2014/0316305 A1 | 10/2014 | Venkatraman | |
| 2015/0012132 A1 | 1/2015 | Francis, Jr. | |
| 2015/0019266 A1 * | 1/2015 | Stempora | G06Q 40/08 705/4 |
| 2015/0289217 A1 * | 10/2015 | Ban | H04W 56/001 455/41.2 |
| 2016/0143544 A1 * | 5/2016 | Tanaka | A61B 5/0015 600/479 |
| 2016/0360980 A1 * | 12/2016 | Sinha | G16H 30/40 |
| 2017/0042485 A1 * | 2/2017 | Chung | G06F 1/163 |
| 2018/0007315 A1 * | 1/2018 | Kim | H04N 5/23222 |
| 2018/0052896 A1 * | 2/2018 | Kim | G06Q 10/109 |
| 2018/0322248 A1 * | 11/2018 | Alisuag | G16H 10/60 |

OTHER PUBLICATIONS

Wi-Fi Positioning System, Wikipedia, Jun. 21, 2016, 5 pages.
International Preliminary Report on Patentability from corresponding International Patent Application No. PCT/EP2017/064165, completed Aug. 7, 2018, 13 pages.

* cited by examiner

Fig. 9

USING A MOBILE PHONE FOR MONITORING A MEDICAL DEVICE

FIELD OF THE INVENTION

This invention relates to a method and a system for monitoring the health of a portable medical device, by, for example, determining if the medical device needs to be replaced or serviced.

BACKGROUND

Portable or wearable medical devices are used to treat or alleviate a number of illnesses. Examples of such medical devices include injection devices, infusion devices, blood glucose meters and dialysis devices.

The number of injectable medicaments that are self-administered by patients is constantly growing. Insulin is perhaps the most well-known example of a medicament that the patient injects himself, but in addition also antibodies, growth hormone, EPO, and certain chemotherapy drugs are self-administered by the patient by injection.

Injection is most frequently done with a handheld injection device, which typically is used from one to six times per day (as opposed to an infusion device that continuously deliver a medicament).

Such medicaments can also be delivered by a portable infusion pump that is more or less permanently connected to the patient.

Dialysis can be carried out with portable or wearable dialysis machines that are carried by the patients.

It is of great importance, for patient safety reasons, that portable or wearable medical devices work in a correct and dependable manner. At the same time, such devices, which are carried by the users at all times, may be exposed to extreme temperatures or humidity, or shock (if the user drops the device), or other harmful conditions which may damage the device.

Such medical devices may malfunction from time to time, and they may then need service or replacement.

SUMMARY OF THE INVENTION

In a first aspect of the invention there is provided a method involving a portable medical device, being carried by a user and client device which preferably is a portable client device, such as a mobile phone, carried by the same user, the method comprising the steps of: a) the client device at a time point (first time point) determining a geographical position of the client device, and providing the geographical position and the first time point to a server via a data connection, or the client device at a first time point having its position determined by the cell network, and the cell network providing the position and the first time point to the server, then b) the server using the position and the time point to retrieve position-specific data for the time point, then c) the server using a the position-specific data from step b. to determine whether the medical device should be serviced or replaced.

The invention has several advantages. One advantage is that there is provided novel means for monitoring a portable medical device. It may be critical to the health of the user that the portable medical device works correctly. Therefore it may be very useful to replace or service the medical device before the medical device breaks down. The invention provides a method, a system, a client device and a server that makes it possible to continuously detect if the medical device has been exposed to harmful conditions, such as extreme temperature or humidity.

The invention enables the monitoring of the medical device, with regarding to which environment the medical device is exposed to. This may be particularly useful when the medical device is not battery powered, since such a medical device cannot have powered sensors.

By relying on data provided by an external provider of data (or sensors in the mobile phone) the medical device does not have to have sensors of its own. Moreover, certain types of data that cannot be detected by commonly used sensors can be used for monitoring the medical device, for example traffic density or people density.

By relying on the position of the client device (mobile phone), the medical device does not have to be switched on in order to determine the position. This saves battery in the device. It is important to save the battery of the medical device because if the battery of the medical device is not charged, the patient cannot carry out critical treatments, thereby putting the patient at risk.

In a preferred embodiment the medical device has an operations sensor, a processing unit and a memory and wireless communication device, which preferably is a cell phone transceiver, integrated in a housing and is able to store information in the memory about time points for operation events, and the method involves, carrying out step a) by: i) the client device determining the geographical position for the client device for at least a first time point and a second time point, and transferring these positions and time points to the server via a data connection, or the client device having its position determined for at least a first time point and a second time point by a cell network, and the cell network providing the positions and time points to the server, ii) the medical device determining, using the operations sensor, a time point for when the medical device has been in use (third time point), iii) the medical device, using its cellular radio transceiver (or other means, such as Wi-Fi), establishing a data connection to the server and transferring the third time point to the server, and iv) the server selecting, among at least the first time point and the second time point, the time point that is closest to the third time point and the server in step, b) using the time point selected in step iv) for retrieving position-specific data. The position may be determined for a plurality of time points and the selection in step iv) can be made from the plurality of time points. The data connection between the medical device and the server is at least partially wireless, such that no physical connector has to be connected to the medical device in order to establish the data connection. In a preferred embodiment the medical device uses a cellular radio transceiver.

It is likely that the medical device is more prone to damage when it is in use. This embodiment has the advantage that position-specific data for the time of operation of the medical device can be used for monitoring the medical device.

The cell transceiver of the medical device can be used to transfer information about, for example, injections to the server (for example for monitoring patient compliance), while at the same time saving battery of the medical device. In this way the medical device does not have to switch on the cell transceiver often, perhaps only once per day, thus saving battery of the medical device.

Step i) is preferably carried out by the client device (mobile phone) establishing the position for at least a first time point and a second time point.

The medical device may be configured to carry out step iii), i.e. the transfer of time points for operation at least at predetermined time intervals. The medical device may be configured to carry out this step automatically after the medical device has been in use. This has the advantage that use data may be transferred and used at the server for monitoring patient compliance. That data is most useful if it is transferred rather rapidly after use.

The position-specific data can be provided by an external provider of data, for example a weather service. The position-specific data may be one selected from the group consisting of a air pressure, humidity, temperature, or other weather or climate parameter, traffic, air pollution, air particle density, air pollen density and person density (for example people per area unit). The position-specific parameter may be altitude above sea level for a position determined by latitude and longitude.

The determination step (step c) may involve the server establishing if the position-specific data is a value that exceeds a threshold value.

Machine learning can be used for obtaining a decision rule for the determination step. Thus, the determination step (step c) may involve the server applying a decision rule, said decision rule being generated by applying machine learning to a data set, said data set comprising previously collected position-specific data for comparable medical devices, said data set also comprising data about previous failures of the comparable portable medical devices.

In preferred embodiment the portable medical device is a device for injection of a medicament (thus not an infusion device).

The mobile phone may comprise instructions such as software (an app) that causes the mobile phone to determine the position at least every predetermined time period.

The position can be established by the mobile phone in different ways. In one embodiment the position is determined by the mobile phone using GPS or other similar satellite based system. In one embodiment the position is determined by the mobile phone using Wi-Fi positioning (WPS). The geographical positions may be provided to the server from the mobile phone via a data connection provided by the cell network.

In a preferred embodiment the position of the mobile phone is determined by the cell network. A cell network can determine the position of a mobile phone with a sufficient accuracy to retrieve position-specific data. This saves the battery of the mobile phone. Also, software for the purpose of timing position determination does not have to be installed in the mobile phone.

In a second aspect of the invention there is provided a system comprising a portable medical device being carried by a user and a mobile phone carried by the same user, a cell network and a server, the mobile phone being configured to determine and store the geographical position of the mobile phone together with a time point for determination of said geographical position and to provide the geographical position and the time point to a server via a data connection, or the cell network being configured to determine the position of the mobile phone, the cell network being configured to provide the position and the first time point to the server, the server being configured to use said position and said time point to retrieve position-specific data for the time point, and to use the position-specific data to determine whether the medical device should be serviced or replaced.

In one embodiment the medical device of the system has an operations sensor, a processing unit and a memory and a cell phone transceiver integrated in a housing and is able to store information in the memory about time points for operation events, and where the mobile phone is configured to determine the geographical position for the mobile phone for at least a first time point and a second time point, and transferring these positions and time points to the server via a data connection, or the cell network is configured to determine the position of the mobile phone for at least a first time point and a second time point and to provide the positions and time points to the server, the medical device being configured to determine, using the operations sensor, a time point for when the medical device has been in use (third time point), and to, using its cellular radio transceiver, establishing a data connection to the server and transferring the third time point to the server, the server being configured to receive at least the first, second and third time points and to select, among at least the first time point and the second time point, the time point that is closest to the third time point and to use the position of the selected time point to retrieve position specific data for the for the time point, and to use the position-specific data to determine whether the medical device should be serviced or replaced.

The medical device may be configured to establish a data connection to the server and transfer the third time point to the server at least at predetermined time intervals. The medical device may be configured to establish a data connection to the server and transfer the third time point to the server automatically after the medical device has been in use.

The mobile phone may comprise instructions that causes the mobile phone to determine the position at least every predetermined time period. The predetermined period can be at least once per day.

In a third aspect of the invention there is provided a server having stored thereon information associated with an identified portable medical device, the server being configured to receive a position and a time point of a mobile phone, and configured to use the position and the time point to retrieve position-specific data for the time point, and to use the position-specific data to determine whether the portable medical device should be serviced or replaced.

The server may be configured to receive at least a first time point associated with a first position for the mobile phone and a second time point associated with a second position for the mobile phone and receiving, from the portable medical device a time point for when the medical device has been in use (third time point), the server having time point selection software that selects, among at least the first time point and the second time point, the time point that is closest to the third time point, the server being configured to use the selected time point and position to retrieve the position-specific data.

In a fourth aspect of the invention there is provided a mobile phone having stored thereon information about an individual portable medical device, the mobile phone being configured to determine and store the geographical position of the mobile phone together with a time point for the determination of the geographical position and to provide said geographical position and said time point to a server via a data connection, the mobile phone being configured to receive information from the server whether the portable medical device should be serviced or replaced.

The method may involve providing a portable medical device, said portable medical device being carried by a user, providing a mobile phone capable of determining position or having its position determined, carried by the same user, and the mobile phone at a time point (first time point) determining a position of the mobile phone, and providing the geographical position and the first time point to a server via a data connection provided via at least the cell network.

The method may involve the mobile phone determining the geographical position for the mobile phone for at least a first time point and a second time point, and transferring these positions and time points to the server via a data connection provided via at least cell network, or the mobile phone having its position determined for at least a first time point and a second time point by a cell network, and the cell network providing the positions and time points to the server.

DRAWINGS

The accompanying drawings form a part of the specification and schematically illustrate preferred embodiments of the invention, and serve to illustrate the principles of the invention.

In the figures of systems, the server, both hardware and software components are shown.

Although it is referred to, in relation to injection devices, to "injection", "time of injection", "injection means" "injection device", etc. in this application, it should be understood that an injection also refers to cases when medicament is ejected by the medical device without being injected into a patient. That may be the case, for example, when a user primes a syringe by ejecting a small amount of medicament for the purpose of checking that the device works as intended.

The disclosed threshold values, for example 50° C., are provided as examples only and are not limiting in any way. The actual threshold values to be used when using the invention can be found by carrying out tests, found in specifications for components used in the actual device or by machine learning, as described below. The thresholds are preferably predetermined meaning that the threshold is fixed at least before the server makes the determination step. When it is referred to that data is transferred herein, it is acknowledged that data may also alternatively be "provided".

When referred to a "client device" herein it is preferably a portable client device such as a mobile phone.

DETAILED DESCRIPTION

Figure 1:
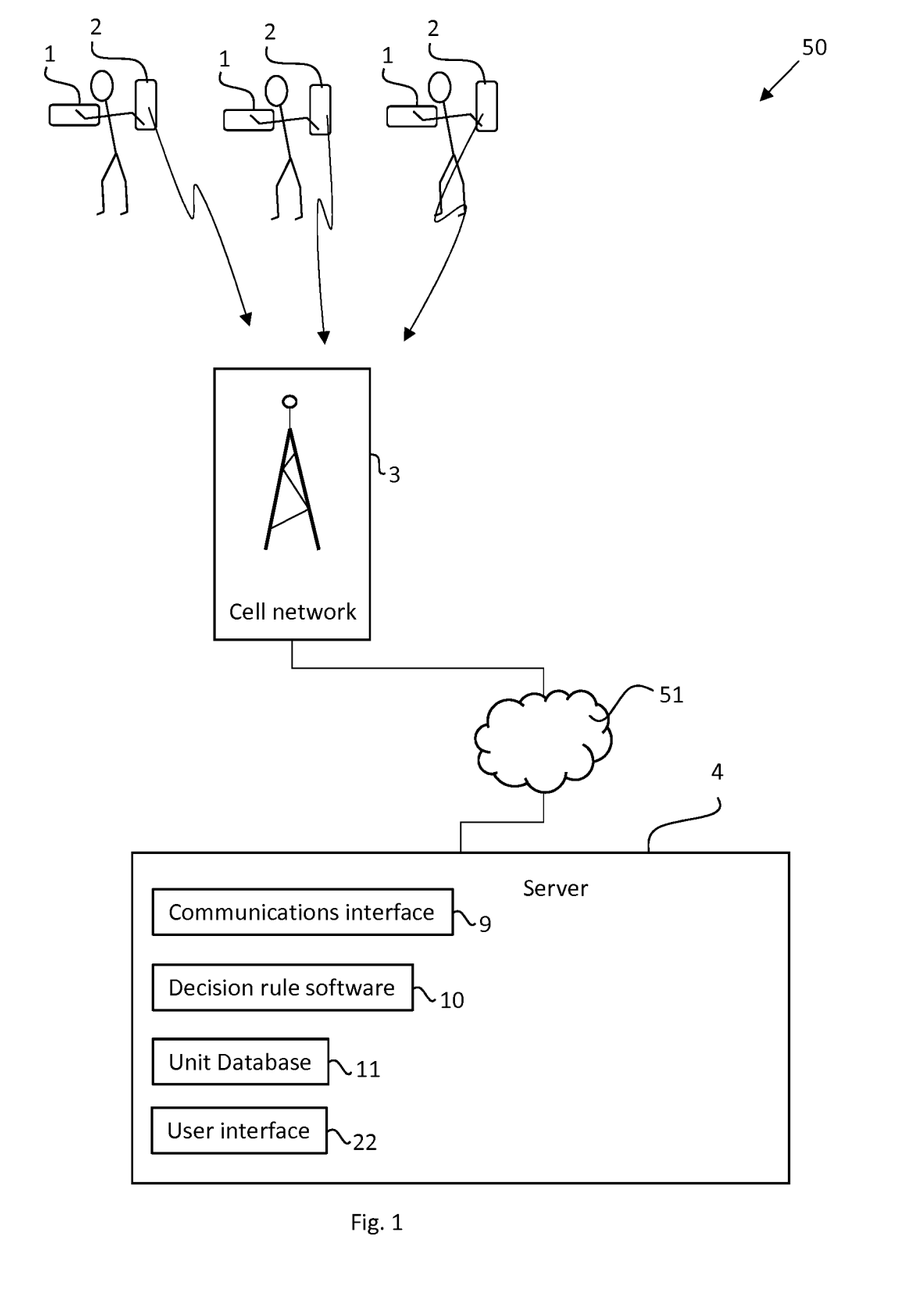
FIGS. 1-3 are schematic drawings of systems.

With reference to FIG. 1, the invention is based on the assumption that the user of a portable medical device 1 simultaneously carries a mobile phone 2. The mobile phone 2 is used for establishing the geographical position of the user and thus the geographical position of medical device 1. The very small position difference (probably less than 1 m) between medical device 1 and mobile phone 2 is thus neglected. The geographical position together with the time point is used for retrieving data for various parameters that may affect the reliability of the device, for example local temperature, or humidity. It is assumed that that local temperature or humidity can affect the behaviour of the medical device 1. For example, if the local humidity is extremely high, the medical device may need service or replacement. Data for a large number of medical devices 1 can be gathered in a dataset 15 to which machine learning can be applied, to identify patterns that can predict device failure.

System 50 comprises the medical device 1, mobile phone 2, cell network 3 and server 4.

Thus, the system 50 preferably includes a plurality of medical devices 1 each associated to one user and one mobile phone 2. The server 4 can be used to monitor a plurality of medical devices 1.

Figure 2:
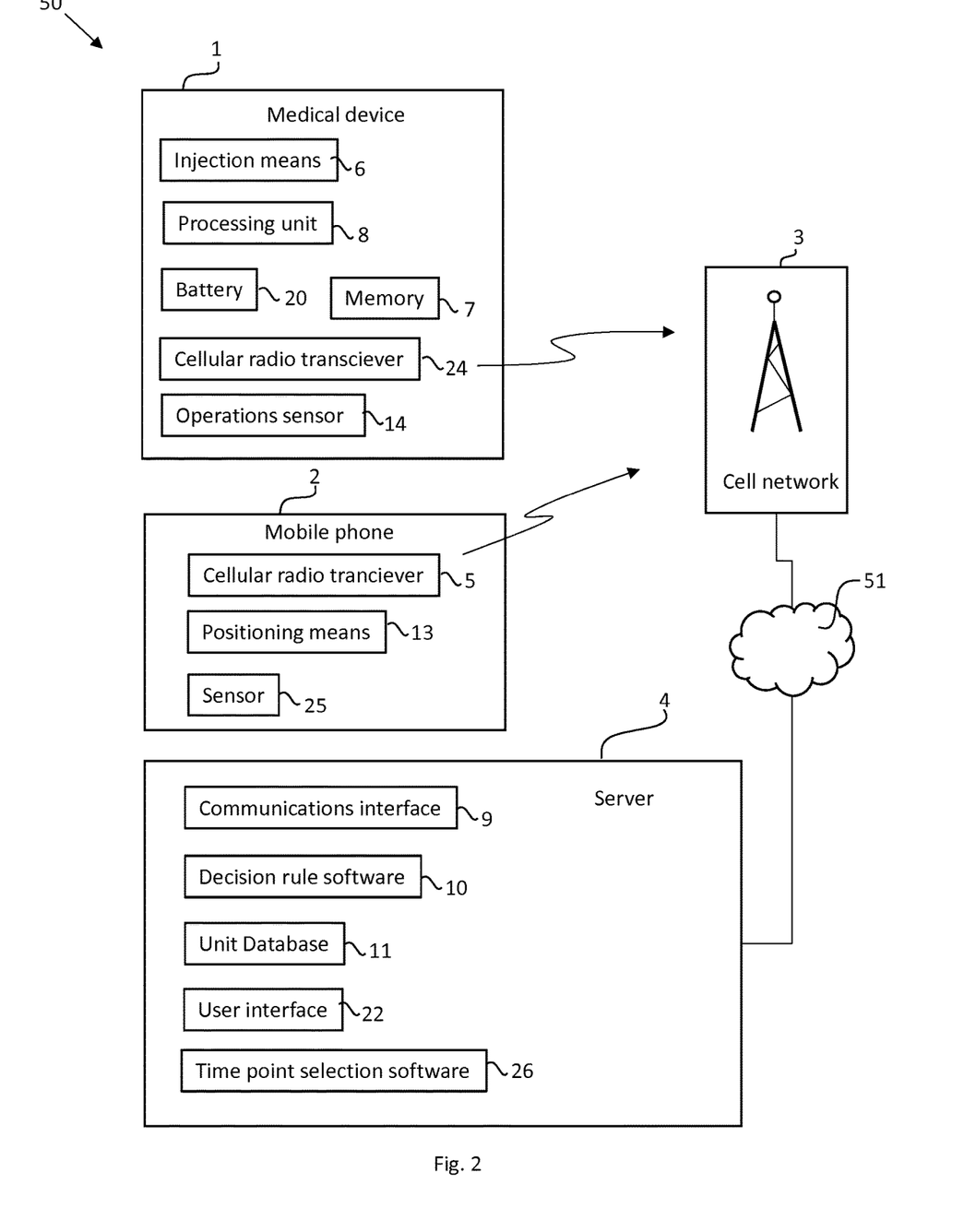

With reference to FIG. 2, the medical device 1 herein may be a portable or wearable medical device such as, for example, a portable device for the injection of a medicament, a blood glucose measuring device, a portable or wearable dialysis machine or a portable or wearable infusion device for the infusion of a medicament such as insulin. The portable medical device may be a handheld medical device.

In a preferred embodiment the medical device 1 is a portable injection device. A portable injection device 1 may be used for the injection of a medicament such as growth hormone, antibodies (such as antibody-based medicaments) or insulin. Typically the injection device 1 is used by a person to inject himself or herself from one to six times per day. Such a portable injection device can be carried by the user, for example in a pocket or in a handbag. This is the most common way for a person to administer insulin to himself or herself, as opposed to an infusion device which is continuously connected to the body of the user and which administers a drug more or less continuously during the day. An injection device administers a medicament at the initiative of the user. An infusion device, at the other hand, is more or less permanently connected to the user and delivers the medicament continuously.

When the medical device 1 is an injection device it has injection means 6. The injections means 6 may be arranged as is known in the art of injection devices. The injection means 6 may comprise a site for attaching a replaceable cartridge that contains a medicament, for example insulin. The cartridge typically has a site for attaching an injection syringe. The injection means 6 also typically comprises a plunger for creating a pressure in the cartridge and a dose setting means that controls how far the plunger will travel. The plunger is powered by a drive mechanism. The injection means 6 also typically comprises an injection actuator, for example a button that can be pressed by the user. This causes movement of the plunger to the extent allowed by the dose setting means. An example of suitable injections means can be found in WO2015076745 and references cited therein.

Optionally, the medical device 1 may have a cellular radio transceiver 24 for communication with a cell network 3 that allows data traffic. The cell network 3 may be for example a GPRS, 3G, 4G, LTE or similar cell network. The cell radio transceiver 24 typically comprises a SIM card —or a site for attaching a SIM card—for identification of the medical device 1 in the cell network 3. The cellular radio transceiver 24 is capable of establishing a data connection between the medical device 1 and a server 4, for example via the internet. However, voice traffic is not necessary and is not necessarily enabled by cell radio transceiver 24. An advantage with communication using cell network 3 over, for example, Wi-Fi, is that cell coverage does not require a manual log-in procedure and is available almost everywhere. Communication between medical device 1 and server 4 may, in addition, involve other types of network of connection types that supports data communication, for example wire-bound technologies.

The medical device 1 may have an operations sensor 14. This sensor 14 is able to sense when the medical device 1 is used, for example by sensing the movement of movable parts of the medical device. The operations sensor 14 can for example be arranged to detect rotation of a rotating part, or the linear motion of a plunger of the injection means 6 of the medical device.

The sensor 14 may for example sense the turning or displacement, expansion or contraction of a part of the medical device 1, or the insertion of consumable part into the medical device 1, temperature change, use of consumable part or material, change of level of a fluid in a compartment or pressure.

Examples of how an operations sensor 14 can be arranged can be found in WO2015076745 and references cited therein. The operations sensor 14 may be able to sense rotation or linear movement. The operations sensor 14 may for example be an optical sensor that detects motion.

When the medical device 1 is not an injection device, but, for example, an infusion device or a dialysis machine, the operations sensor 14 may sense the movement of a pump or a plunger in the medical device 1.

When the medical device 1 is a blood glucose meter the operations sensor 14 may detect the insertion of a test stick in a test stick port.

The medical device 1 may have a memory 7 for storing software and data from the operations sensor 14 and a processing unit 8 for executing software and for communicating with operations sensor 14 of the device. The memory 7 is preferably a solid-state memory. The medical device 1, preferably the processing unit 8, may have a clock for determining time points. The processing unit 8 may able to generate error codes if parts of the medical device malfunctions. Error codes may relate to, for example, that the battery does not charge, loss of communication with parts of the device, processing unit failure, memory failure or sensor failure.

The portable medical device 1 may preferably be powered by a battery 20, thus being a battery-powered device. The processing unit 8, memory 7 and cellular radio transceiver 24 may be powered by battery 20. The battery 20 may also power operations sensor 14. Battery 20 may also power pumps or engines or sensors (for example a blood glucose sensor) that is necessary for the operation of medical device 1.

The medical device 1 may comprise a digital log of operations of the medical device. When the medical device 1 is an injection device it may comprise a log of injections that is carried out and thus keep track of the injections made by the user. The digital log may also log blood glucose values when the portable medical device comprises a blood glucose measuring device.

The medical device 1 may also have a user interface that includes a display. The medical device 1 preferably has a housing that includes the various components of the medical device 1. The processing unit 8 may be configured to switch off the medical device 1 or put the medical device 1 in sleep mode if it is not used during a pre-determined time, in order to save battery power.

The time points for the use of the medical device 1 may be detected by processing unit 8 registering each time operations sensor 14 sends a signal regarding an operation to processing unit 8. The time point may be stored in digital form in the memory 7 of device 1.

The processing unit 8 may be able to retrieve the time points from the memory 7 and transfer these to the server 4 with aid of cellular transceiver 24 using data communication.

The operations sensor 14, when present, is connected to processing unit 8 such that signalling can occur between these. Sensor measurement, sensor signal processing, and communication between the sensor 14 and the processing unit 8 and memory 7 can be carried out in any suitable manner known in the art of sensor technology. Signal processing and data storage may be carried out in various parts of device 1 such as in sensor 14, memory 7 and processing unit 8.

The mobile phone 2, preferably has a cellular radio transceiver 5 as is known in the art of mobile communication. It is thus able to communicate with a cell network 3. It is preferred that the mobile phone 2 supports voice traffic, for example voice traffic over GSM. Voice traffic may be useful if the user, which may be a diabetic, needs help, for example if hypoglycaemia occurs. The user may need to call the health provider that provides the medical device 1. The mobile phone 2 has a processing unit, a memory and a user interface (for example a touch screen with possibility to enter text and digits). The memory can be used for storing data and software. The cellular radio transceiver 5 typically comprises a SIM card—or a site for attaching a SIM card—for identification of the mobile phone 1 in the cell network 3. The mobile phone 2 may have a Wi-Fi chip (circuit) which can be used to connect the mobile phone 2 to a Wi-Fi network. The mobile phone 2 may have a GPS chip for receiving signals from satellites 52 for positioning.

Mobile phone 2 may be able to establish a data connection to server 4. Communication between mobile phone 2 and server 4 can be carried out with any suitable technology such as a cellular network (3G, 4G, LTE and the like), or Wi-Fi. Suitably a wireless technology is used. Communication between mobile phone 2 and server 4 may occur via a wide area network such as the internet 51. Communication between mobile phone 2 and server 4 may also for example occur by the mobile phone sending a text message (SMS) to the cell network 3 which in turn sends the information to the server 4. When for example Wi-Fi is used to transfer the time point and the position it may not be necessary to involve cell network 3 in this step.

It is also preferred that the user interface of mobile phone 2 has a display for showing images and text. The display is preferably a touch display. The touch display may be able to show a keyboard which makes it possible for the user to input information to the mobile phone 2. It is also preferred that the mobile phone 2 allows download and installation of software, for example apps. Examples of suitable mobile phones (client devices) 2 are IPhone and Android phones.

The mobile phone 2 may have at least one sensor 25. The sensor may be one of a temperature sensor, humidity sensor, air pressure sensor, a light sensor and an acceleration sensor. The sensor 25 can be used in a separate embodiment of the invention, described below.

Figure 3:
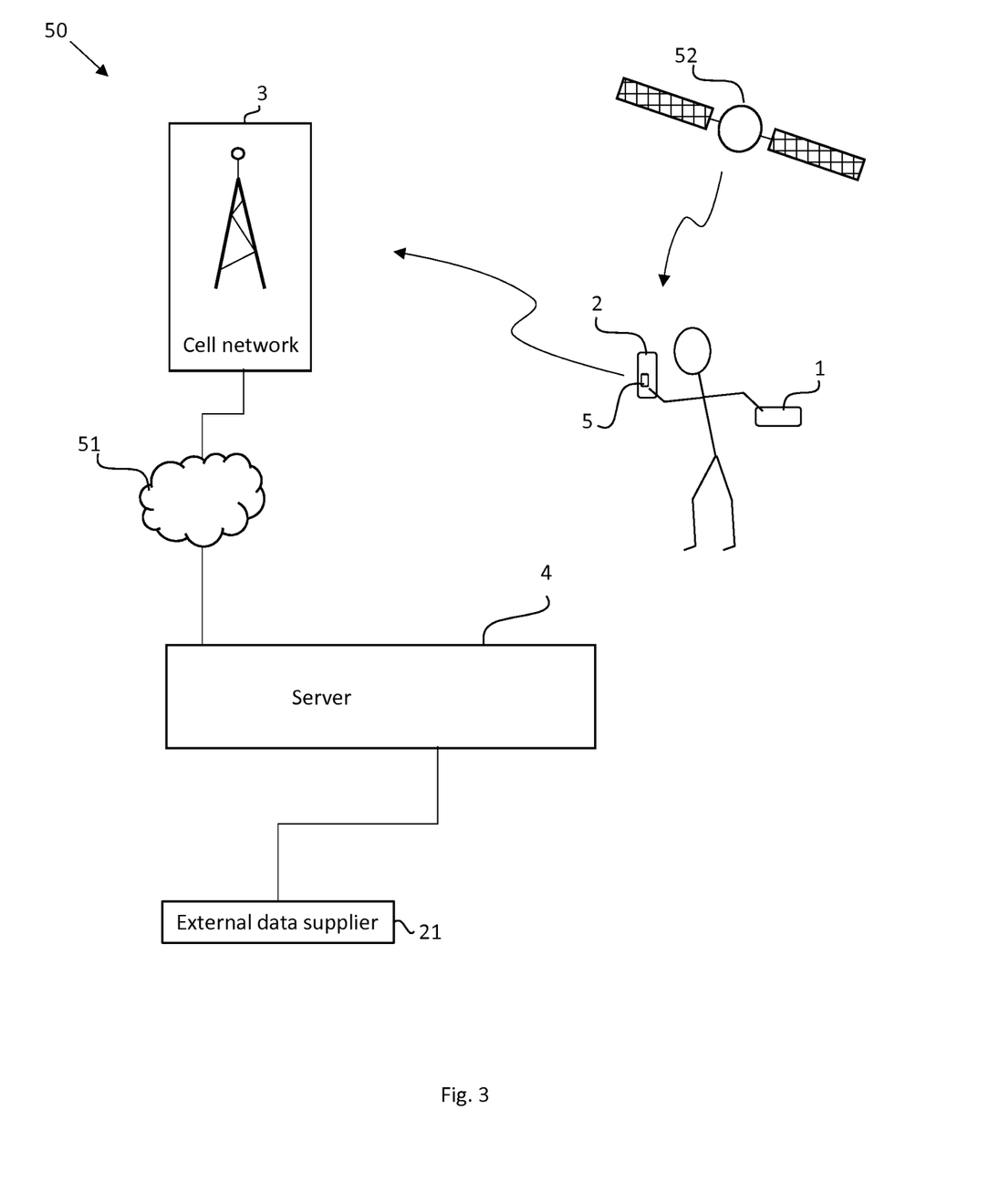
Figure 6:
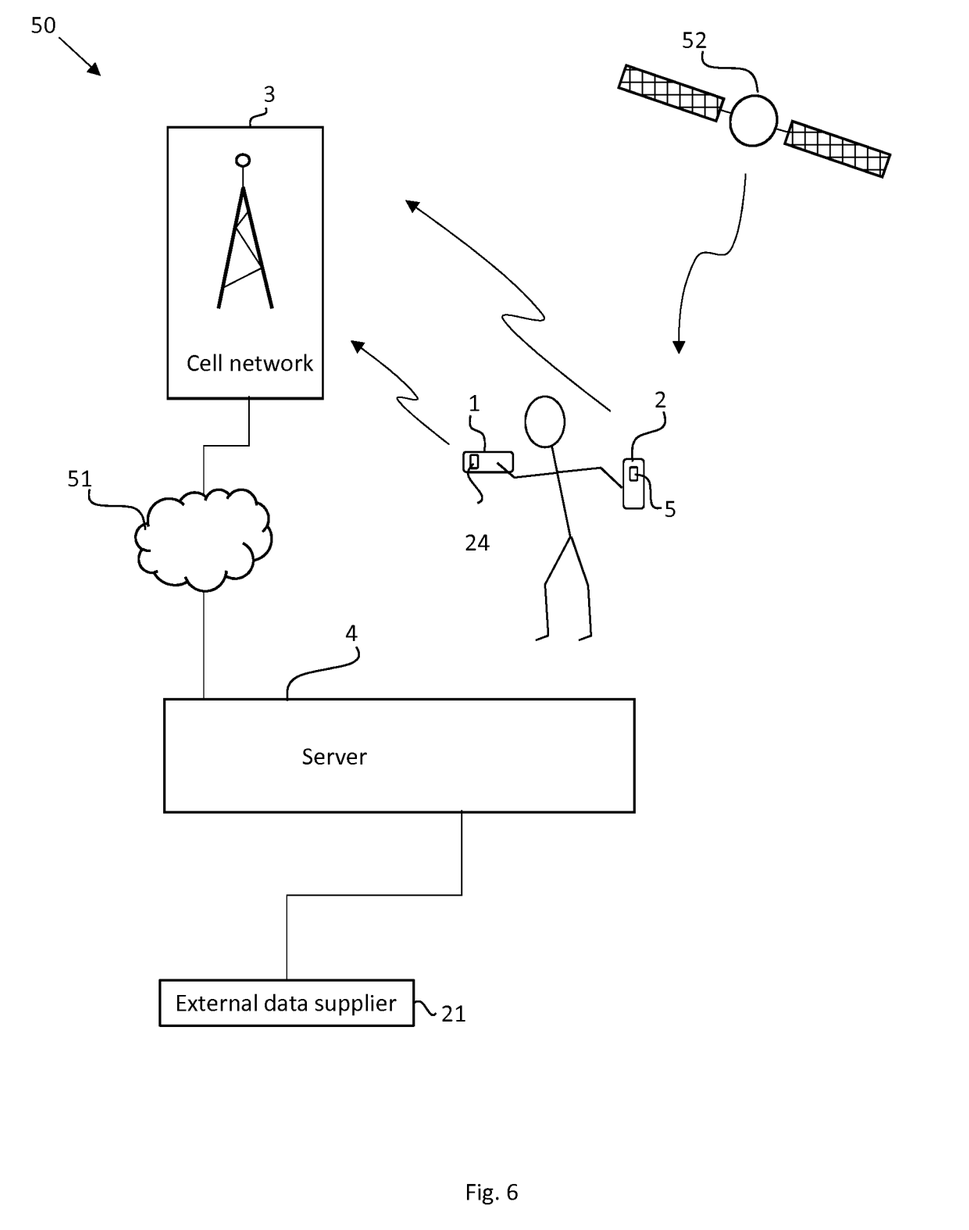
FIG. 6 is a schematic drawing of a system.

The mobile phone 2 is able to establish the geographical position of where it is currently positioned, or having its position determined by cell network 3. This can be done with any suitable technology, including GPS, mobile phone tracking or Wi-Fi positioning. Thus, the mobile phone 2 may have positioning means 13, for example a GPS positioning means that can receive signals from a satellite 52 (FIGS. 3 and 6). The geographical position may for example be expressed using latitude and longitude.

The mobile phone 2 may have software (for example an app) that automatically makes the mobile phone 2 determine the position and store the position together with a time point in the memory of the mobile phone 2. This can be repeated on at least suitable predetermined time intervals, for example at least every 15 minutes. The software (app) of the mobile phone 2 can determine this time interval, and a clock or timer in mobile phone 2 can be used for determining time. The app may also provide instructions to the mobile phone 2 to transfer the position to the server 4, for example at predetermined time intervals, which may be longer than the time interval for determining position, for example once per day. The app in the mobile phone 2 may also be able to provide notifications from the server 4 to the user, for example if the medical device 1 should be serviced or replaced. The mobile phone 2 may have stored in its memory information about the medical device 1, for example the identity of the medical device 1, or the identity of the user.

When mobile phone tracking is used, the position of the mobile phone 2 is determined by the cellular network 3. The cellular network 3 may use information about which cell the mobile phone 2 is connected to, or may use multilateration involving several cells. The cell network 3 may comprise a database of mobile phones for which position should be determined. The positions of the mobile phones are stored in the database, and made available to the server 4. The cell network 3 may comprise instructions to determine the positions of the mobile phone 2 at predetermined intervals. Thus computers of the cell network 3 may be configured to determine the positions of a mobile phone 2 or a group of mobile phones 2 at intervals.

The position data is sent from the cell network 3 to the server 4 in any suitable manner. For example the server 4 may query a computer or database of the cell network 3 for geographical data regarding a particular mobile phone 2, or for a plurality of mobile phones 2. The server 4 can store the position data in the database 11.

When GPS or Wi-Fi positioning is used the position may be sent from the mobile phone 2 to the server 4 using a data connection that is established between the mobile phone 2 and the server 4.

The server 4 is typically operated by a healthcare provider, a hospital or a health care providing company. The server 4 has a memory for storing software and data. The server 4 further has a processor and is able to execute software, and it may have an operating system. The server 4 has an user interface 22 for allowing a user at the health care provider to change the settings of the server, for example changing thresholds or receiving notifications. The server 4 has a communication interface 9 for communicating with the mobile phone 2 and/or cell network 3. In some embodiments, the server 4 receives the position of the mobile phone 2 from cell network 3 without the server 4 communicating with the mobile phone 2. The communications interface 9 may also be used for communication with medical device 1. The server 4 may be a remote computer. The server 4 may be two or more computers or servers that cooperates, for example as a virtual server.

The server 4 can receive position data from the mobile phone 2 or cell network 3 through the data connection with use of communication interface 9. Preferably the server 4 can retrieve or otherwise obtain data for a plurality of users each carrying one mobile phone 2 and at least one medical device 1.

The server 4 also comprises a database 11 that comprises the identities of a plurality of medical devices 1 and mobile phones 2. Each medical device 1 has a unique identity that may be, for example, a number, a combination of letters or a combination of numbers and letters. Each mobile phone 2 also has a unique identity which may be the mobile phone number or the IMSI number. In the database 11, the identity of each medical device 1 is connected to the identity of one mobile phone 2.

Thus it is ensured that data from a particular mobile phone 2 is connected to a particular medical device 1 in the database 11.

The server 4 has decision rule software 10 for making a decision about the medical device 1. The decision may be if the medical device 1 should be or serviced, scrapped or replaced, or that no action should be taken. The decision rule software 10 may comprise a threshold value for a position specific parameter. Thus, there may be a threshold for each of, for example, temperature, humidity and air pollution. As a hypothetical example, the decision rule may state that if a threshold is over a value (40° C.) on at least a predetermined number of occasions, for example three occasions, the medical device should be replaced. The decision rule software 10 may be updated if needed. For example, a threshold value may be adjusted upwards or downwards by updating the decision rule software 10. This may be done with the use of user interface 22.

The threshold or thresholds in the decision rule software 10 may be altered when it is necessary to do so. For example, if it is discovered, based on experience, that a threshold for temperature should be lowered, this can be done in a convenient manner by the health provider by simply changing the threshold value in the decision rule software 10 of the server 4.

The server 4 may have time point selection software 26 which is described below.

Typically, the medical device 1 is personal i.e. it is used by one person only. The database 11 preferably includes information that allows a health provider to get in touch with the user of the medical device 1, such as phone number, email address or home address. For example, the health provider may decide that a certain medical device 1 needs service or replacement, and then needs to inform the user regarding this.

The server 4 may use cell network 3 and/or a data connection to mobile phone 2 to send a signal to the mobile phone 2 that the medical device 1 needs service or replacement. Such a signal may be in the form of a SMS/text message or via an app in the mobile phone 2. There may also be a sound notification and/or a vibration at mobile phone 2.

The server 4 may use a data connection to medical device 1 to send a signal to the medical device 1, the signal causing the medical device 1 to notify the user of the medical device that the medical device 1 needs service or replacement. The signal from the server 4 may cause the medical device 1 to carry out a systems check, for example check battery power. The signalling may preferably occur in the same communication session between the medical device 1 and server 4 which is used for transferring the operation data to the server 4. Alternatively, this occurs in a later communication session. The notification to the user may be a message displayed on a display of the medical device 1, or a sound signal, or vibration, or a combination of these, or by shutting down the medical device 1. The message on the display may be for example "Error" or "Service" or "Contact health provider X", or "Call XX-XXXXX". The medical device may thus have a user interface, that may include a display, that can be used for the notification.

Figure 4:
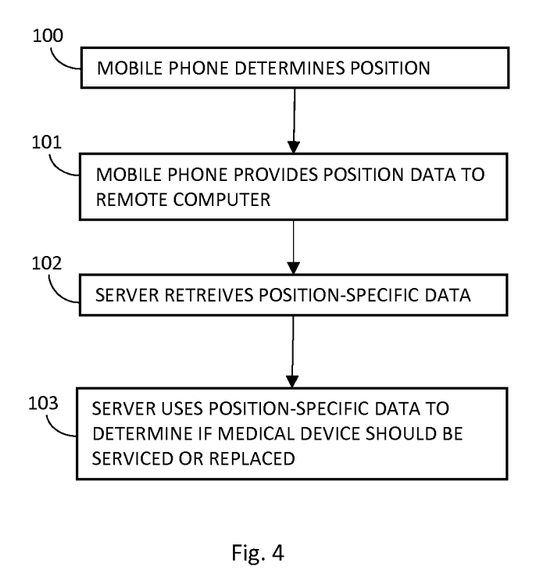
FIGS. 4-5 are flowcharts showing methods.

With reference to FIGS. 3-4, the server 4 is able to use the geographical position of mobile phone 2 together with the time point to retrieve position-specific data for the position of the user and thus of the medical device 1, and use this position-specific data to make a decision if the medical device 1 should be serviced or replaced. The medical device 1 may or may not have each of operations sensor 14, cell transceiver 24, memory 7 processing unit 8 and battery 20.

In step 100 of FIG. 4 the mobile phone 2 determines its position, or, alternatively, the position of the mobile phone 2 is determined by cell network 3. This can be done with the methods that are described above. The position is determined for a first time point. The mobile phone 2 may have software (for example an app) that automatically makes the mobile phone 2 determine the position and store the position together with a time point in the memory of the mobile phone 2. This can be repeated on at least suitable predetermined time intervals, for example at least every 15 minutes. This provides for continuous monitoring of the medical device 1. The software (app) of the mobile phone 2 can determine this time interval, and a clock or timer in mobile phone 2 can be used for determining time. Alternatively, the cell network 3 is configured to determine the position of the mobile phone at predetermined time intervals, for example once every 15 minutes.

The predetermined time interval may be for example from at least every 5 minutes to at least every 24 h. A suitable time interval may be at least every 15 minutes or at least every hour.

In step 101 the mobile phone 2 transfers the position and the time point for the position to the remote computer 4 using a data connection. The mobile phone 2 may first identify itself to the server 4. Identification may be carried out in any manner known in the art. This enables the server 4 to associate position data from the mobile phone with the correct medical device 1 in the database 11. The position data is transferred to the server 4 on at least suitable (longer) predetermined time intervals points, for example once per day, twice per day, four times per day or once per hour. Alternatively, the cell network 3 provides the position of mobile phone 2 directly from cell network 3 to server 4, for example based on which base station or base station mobile phone 2 is connected to. The cell network 3 can do this at predetermined time intervals, which may be for example once per day. The server 4 can query the cell network 3 for position of mobile phone 2 at predetermined time intervals.

In step 102 the server 4 uses the time point to retrieve position-specific data for position and the time point (first time point). The position-specific data may be a value of a parameter, for example one of temperature, air pressure, humidity, traffic, air pollution, and people density for the position. The position-specific data can be retrieved from an external supplier of data 21. The external supplier of data can be any provider or data base that comprises position-specific data. Information about weather, temperature, air pressure, humidity and air pollution can be retrieved, for example, from a weather service. Information about traffic or people density may be retrieved from for example Google. Position-specific data may also be provided from a separate database in server 4. How such information can be used to predict the wear of the device is explained below. If there is not position specific data (say temperature) for a time point that exactly matches the time point of the first time point (and this may often be the case), the server 4 or external provider 21 may select position specific data for the time point that is closest to the first time point.

In step 103 the server 4 uses the position-specific data to decide if the medical device 1 should be serviced or replaced. The server 4 uses decision rule software 10 to do this. The decision rule of the decision rule software 10 may be a threshold. For example, that if a medical device 1 is subjected to temperatures of higher than 40° C. it should be replaced. Naturally the most frequent decision will be to take no action and to allow continued use of the medical device 1.

Say, for example, that a particular medical device 1 should not be exposed to temperatures higher than 40° C. Therefore the threshold is set to 40° C. For example, if the user is located in New Delhi and the time point is 11.45, the server 4 uses this information to retrieve temperature data for 11.45 (or a time point that is close to 11.45) for this position in New Delhi. The temperature data for that time and position was 42° C. Since this value is warmer than 40° C., the server 4 decides that the medical device should be replaced. Similar thresholds can be used for minimum temperature, air pressure, etc.

The service or replacement decision does not have to be made immediately. The method can be used for monitoring a fleet of medical devices over time, and decide to service or replace one or more medical devices at the same time, which can be substantial time after a medical device 1 has been subjected to a harmful condition.

Figure 5:
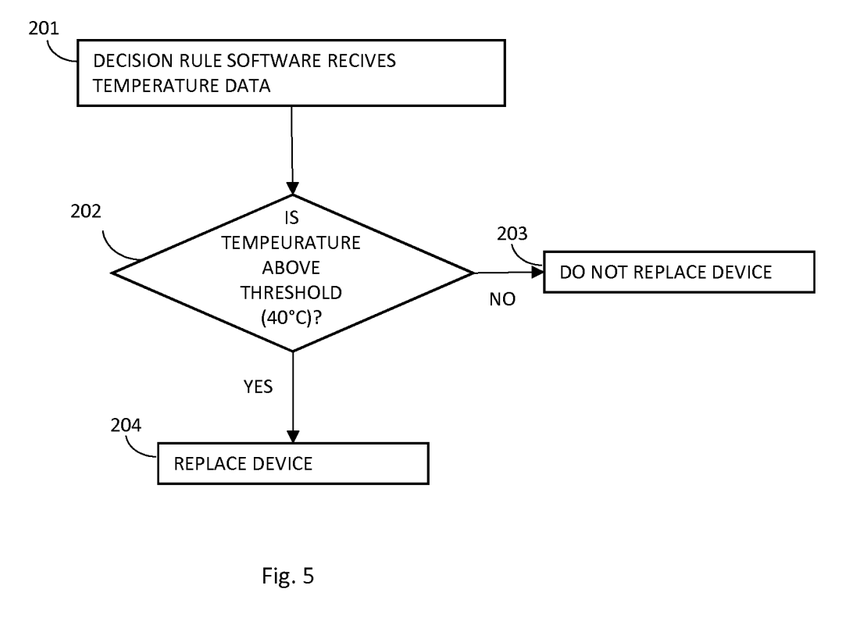

An example of a method involving a decision rule with a threshold is shown in FIG. 5. In step 201 the decision rule software 10 of the server 4 receives position-specific data, in this case a temperature. In step 202 the decision rule software 10 applies the decision rule. In this case the decision rule is that if a temperature of above 40° has been provided to the server 4, for example by external provider 21, the medical device 1 should be replaced. If the recorded temperature value is found, in step 202, to be below or equal to 40° a decision is taken not to replace the device in step 203. If the temperature value from external provider 21 is above 40° C. a decision is taken in step 204 to replace the medical device 1. Thus if the medical device has been subjected to a temperature of above 40° a decision is taken by decision rule software 10 in step 204 to replace the device.

The decision rule may be more complex, and involve more than one parameter, as described in the hypothetical examples below.

The output from the decision rule software 10 can be communicated from server 4 by using the communications interface 9 and/or user interface 22. The user interface 22 may provide a notification regarding replacement, scrapping or service of the medical device 1. Such a notification can be in any suitable form. The notification may be sent to a computer system that keeps tracks of a plurality of medical devices 1. Such a computer system may take the relevant action, for example, automatically ordering a new device, notifying or warning the user of the medical device 1, or notify or warn medical or technical staff. A notification can suitable sent to the mobile phone 2 for example by text/SMS or to an app in the mobile phone 2.

In a separate aspect of the invention, the geographical position is not necessary established. Instead a sensor 25 of the mobile phone 2 is used as proxy sensors for the medical device 1.

Mobile phones adapted for Android or iOS frequently have one or more of the following sensors: air pressure sensor, temperature sensor, accelerometer, humidity sensor and light sensor. Thus in this aspect it may not be necessary to obtain data from an external supplier of data 21. With reference to FIG. 4 step 100 is not necessarily carried out, instead mobile phone 2 uses sensor 25 to determine the value of a parameter selected from air pressure, temperature, acceleration, humidity and light or another parameter that can be sensed by sensor 25 of mobile phone 2. The value is stored in the memory of the mobile phone 2.

Instead of, step 101, the value of the parameter determined by sensor 25 is transferred to the server 4 using a data connection between mobile phone 2 and server 4. Step 102 of FIG. 4 is not carried out. Step 103 is carried out as in FIG. 4. Sensor 25 may determine the value of the parameter at least at predetermined time intervals. This may be controlled by software in the memory of mobile phone 2, for example an app.

Figure 7:
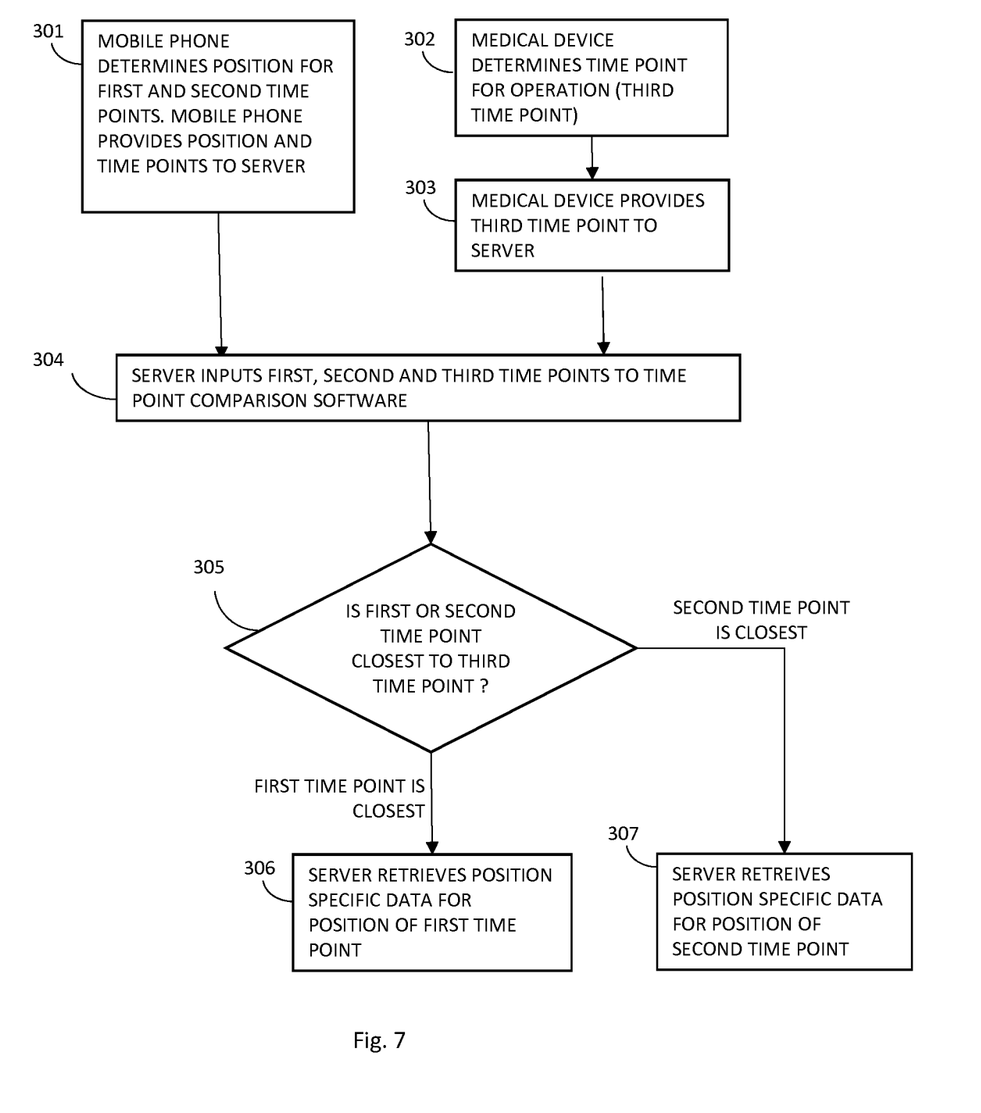
FIG. 7 is a flowchart showing a method.

With reference to FIG. 6-7, when the medical device 1 has an operations sensor 14 for detecting the use of the medical device 1 the method may involve the step of pairing a time point of operation event of medical device 1 with a time point for a geographical position. It is of particular interest to determine the position-specific data for time points when the medical device 1 is in operation, for example when an infusion pump is running or injection is taking place.

Position data can be sent to the server 4 from the mobile phone 2 and paired with a sensor measurement, for example by operations sensor 14, by comparing time points. Thus the server 4 can select the geographical position as determined by the mobile phone (or determined by cell network 3) that is closest in time to the time point of an operation event FIG. 6 shows a system 50 where mobile phone 2 has a cellular radio transceiver 5 (first cell transceiver) and medical device 1 also a cellular transceiver 24 (second cell transceiver). The medical device 1 can use the second cellular transceiver 24 to establish a data connection to server 4, and transfer data to server 4 about time points for use (operation events) of medical device 1.

With reference to FIG. 7. In step 301, the mobile phone 2 preferably determines position, for example using GPS or Wi-Fi positioning, and transfers or provides this position and the time point to the server 4 using data communication. This is done at least at predetermined time intervals as described above for steps 100 and 101 in FIG. 4. This results in that at least first and second time points are received by server 4 from mobile phone 2. Alternatively, the position of the mobile phone 2 is determined by the cell network 3 in which case the positions are provided to the server 4 by the cell network 3. Thus, there will be stored in the server 4, at least a first time point associated with a first geographical position and a second time point associated with a second geographical position. Thus there will be a plurality of time points associated with geographical positions stored in the server 4. It is off course likely that there will be more than two time points.

In step 302, the user of medical device 1 uses the medical device 1, for example by making an injection. This is detected by operations sensor 14. The time point for this (third time point) is determined by clock of medical device 1 and the time point is stored in memory 7. Thus use of the medical device is detected by operations sensor 14. The use of the medical device may be defined as movement of a movable part as detected by sensor 14.

In step 303 the medical device 1 establishes a data connection is established with server 4.

The medical device 1 for example uses cellular radio transceiver 24 to establish a data connection to server 4 via cell network 3. Medical device 1 then transfers the time point of operation (third time point) to server 4. This can be done at predetermined time intervals or immediately after the user has used the medical device 1, for example after making an injection. The transfer of time points may thus be triggered by operation of the medical device 1. For example when the medical device is an injection device, the execution of an injection may trigger the transfer of the time point to the server. If the medical device is a blood glucose meter, the metering operation may trigger the transfer of the time point. If the medical device is a dialysis machine, the completion of a dialysis cycle may transfer the time point of operation. Transfer may occur at least at predetermined time intervals, for example at least once per day, or at least once per hour. The predetermined time interval for transferring operation time points may preferably be longer than the predetermined time interval for when the position of the mobile phone is determined. The operation events may be used for logging the use of medical device 1 for medical purposes, for example for monitoring patient compliance with a therapeutic regiment.

The first, second and third time points are stored in memory of server 4. Step 301 may be carried out before or after step 302 or 303. Steps 301, 302 and 303 may be carried out repeatedly which result in two sets of time points in server 4. In order to pair a time point for operation with the correct geographical position the server carries out steps 304-305.

In step 304 the server 4 provides at least the first, second and third time points to time point selection software 26. The time point selection software 26 in step 305 selects the time point of the first time point and the second time point that is closest to the third time point. Thus, the time point selection software 26 selects, from plurality of time points, that are each associated with a geographical position, the time point that is closest to the time point of operation.

If the first time point is closest, the position of the first time point it is used for retrieving position-specific data in step 306. If the second time point is closest, the position of that time point is used for retrieving position specific data at step 307. Steps 306 and 307 are carried out as step 102 in FIG. 4.

For example, if an operations sensor 14 measurement from medical device 1 takes place at 15.25 (third time point) and there is a position X at 15.00 and a position Y at 1530, the time point selection software 26 of server 4 selects position Y, since it is closest in time to the operations sensor 1 measurement at 15.25. Thus the server 4 uses position Y to retrieve position-specific data.

Yet another example is provided in table 1.

TABLE 1

| Operation time point (third time points) | Time points for positions | Geographic position (Coordinates) |
|---|---|---|
|  | 07.00 | $X_1 Y_1$ |
| 08.22 | 08.00 | $X_2 Y_2$ |
|  | 09.00 | $X_3 Y_3$ |
| 10.03 | 10.00 | $X_4 Y_4$ |
|  | 11.00 | $X_5 Y_5$ |
|  | 12.00 | $X_6 Y_6$ |

In the example of Table 1 positions with coordinates $X_2 Y_2$ is used for retrieving position-specific data. Position $X_4 Y_4$ is also used for retrieving position-specific data.

In a separate embodiment, that can be combined with other embodiments herein, the operation data is transferred from the medical device (1) to the mobile phone 2 wirelessly, for example with the use of Bluetooth or near field communication, and the mobile phone 2 transfers the data to the remote computer 4 as described above. The server 4 then uses the operation event data as described above.

Figure 8:
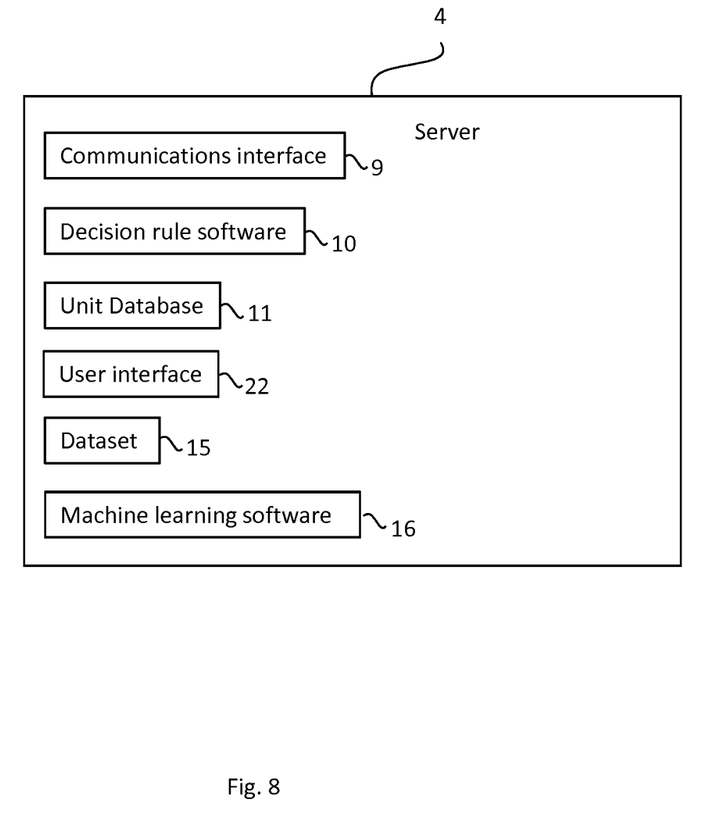
FIG. 8 is a schematic drawing of a server.

With reference to FIG. 8, in a preferred embodiment, the decision rule software 10 implements a decision rule that is generated by applying machine learning to a data set 15, said data set 15 comprising data previously collected from similar portable medical devices, said data set 15 comprising data about any previous failure of the similar devices. Failures includes breakdowns, failure, replacements or error codes of such similar portable medical devices.

"Similar" or "comparable" devices means devises are devices that can be compared for example because they are of the same model or shares certain component in a way that one can reasonable expect that they behave in the same manner.

Machine learning, as such, is previously known. Machine learning may for example involve applying Bayesian networks or artificial neural networks. Guidance can be found in US2014/0012784, US2008/0059120 and U.S. Pat. No. 8,819,498. The server 4 may comprise machine learning software 16 that analyses the data set 15 to produce a decision rule that is implemented in the decision rule software 10. The data set 15 may comprise the information in the unit database 11.

The dataset 15 may comprise any useful information. Thus the data set 15 may include information about model, serial number, address of user, manufacturing day, components and manufacturer of the medical device 1, and previously recorded position-specific data (temperature, humidity, etc.).

Importantly, the dataset 15 comprises information about previous failures of medical devices 1 or similar medical devices. This data may be entered manually. Alternatively the dataset 15 may automatically receive error codes from the medical devices 1 or comparable medical devices. The size of the dataset 15 will increase over time, which will improve the decision rule. The method may involve the step of automatically adding the position-specific data to the dataset 15. The method may involve the step of automatically adding information about error codes from the medical device 1 to the dataset 15.

By applying machine learning to the dataset 15, the decision rule of the decision rule software 10 will be able to take into account previously unknown factors for diagnosing the medical device 1. For example, it is feasible that a certain pattern of use (say high frequency use) together with a low temperature may increase the risk of damage to the medical device. It is possible to detect such a failure pattern by using machine learning. Thus the method can be used as a research tool. Parameters that can be included in the dataset 15 and thus be taken into account when the machine learning software 16 creates decision rule in the decision rule software 10 may include: temperature, humidity, air pollution, usage pattern, error codes, time of day for use or time for generation of error code, model, serial number, address of user, manufacturing day, serial number of components in the medical device 1, and replacement of the medical device 1. Also data from sensor 25 may be used. For example a certain pattern of acceleration may indicate that user is carrying out physical exercise.

By applying machine learning to the dataset 15 new patterns that predict failure of the medical device 1 can be discovered. Such patterns are yet to be discovered but a few purely hypothetical examples are now mentioned for illustrative purposes only. A first hypothetical example is that injection at high temperatures predicts wear of the medical device 1. A second hypothetical example is that a combination of high temperature and high humidity results in failure of the medical device when the medical device has parts from a certain subcontractor. A third example is that injection of volumes over 1 ml causes battery charging error codes.

Preferably the dataset 15 includes data from a large number of medical devices 1, preferably more than a thousand medical devices 1.

The method may comprise the step of the server 4 adding the position-specific data, data from sensor 14 or sensor 25 or time points or positions, position-specific data received from external supplier 21, medical device 1 or mobile phone 2, to the dataset 15.

Figure 9:
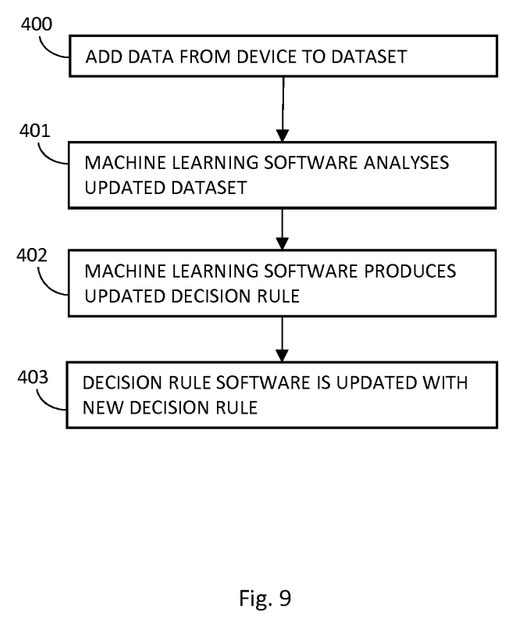
FIG. 9 is a flowchart showing a method.

The method may comprise the step of the machine learning software 16 analysing the updated dataset 15 and producing an updated decision rule, and updating the decision rule software 10 with the new decision rule. This is shown in FIG. 9 which shows how in step 400, the server 4 receives data, for example position-specific data from external supplier 21. The data is then added to the data set 15. In step 401 machine learning software 16 analyses the updated dataset 15, to produce an updated decision rule in step 402. This updated decision rule is then used to update the decision rule software 10 in step 403. The machine learning software 16 may apply a cutoff for providing a decision rule such that a decision rule must have at least a minimum predetermined confidence in order for the decision rule to be used for updating the decision rule software.

Step 403 may be omitted. When step 403 is omitted the decision rule software may be updated manually. The machine learning software 16 may then send a notification to an operator (using user interface 22) who may then update decision rule software automatically.

While the invention has been described with reference to specific exemplary embodiments, the description is in general only intended to illustrate the inventive concept and should not be taken as limiting the scope of the invention. The invention is generally defined by the claims.

The invention claimed is:

1. A method involving a portable or wearable medical device the medical device having an operations sensor, a processing unit and a memory and a cell phone transceiver integrated in a housing and is able to store information in the memory about time points for operation events, the medical device being carried by a user, and a client device carried by the same user, where the client device comprises instructions that causes the client device to determine the position at least at predetermined time intervals or where the cell network provides the position of the client device to a server at predetermined time interval, the method comprising the steps of:
   a) the client device determining the geographical position for the client device for at least a first time point and a second time point, and transferring these positions and time points to the server via a data connection, or the client device having its position determined for at least a first time point and a second time point by a cell network, and the cell network providing the positions and time points to the server,
   b) the medical device determining, using the operations sensor, a time point for when the medical device has been in use (third time point),
   c) the medical device, using its cellular radio transceiver, establishing a data connection to the server and transferring the third time point to the server,
   d) the server selecting, among at least the first time point and the second time point, the time point that is closest to the third time point,
   e) the server using the position and the time point selected in step d) to retrieve position-specific data selected from the group consisting of a weather or climate parameter, air pressure, humidity, temperature, traffic, air pollution, air particle density, air pollen density, person density and altitude above sea level, for the position and the time point, then f) the server using the position-specific data from step e) to determine whether the medical device should be serviced or replaced.

2. The method of claim 1 where step c) is carried out by the medical device at least at predetermined time intervals.

3. The method of claim 1 where step c) is automatically carried out by the medical device after the medical device has been in use.

4. The method of claim 1, wherein step f) involves the server applying a decision rule, said decision rule being generated by applying machine learning to a data set, said data set comprising previously collected position-specific data for comparable medical devices, said data set also comprising data about previous failures of the comparable portable medical devices.

5. The method of claim 1, where the portable medical device is a device for injection of a medicament.

6. The method of claim 1, where the client device determines the geographical positions and transfers the geographical positions and time points to the server via a data connection provided by the cell network.

7. A system comprising a portable or wearable medical device being carried by a user and a client device carried by the same user, a cell network and a server, where the medical device has an operations sensor, a processing unit and a memory and a cell phone transceiver integrated in a housing and is able to store information in the memory about time points for operation events, and where the client device is configured to determine and store the geographical position of the client device for at least a first time point and a second time point, and transfer these positions and time points to the server via a data connection, or the cell network is configured to determine the position of the client device for at least a first time point and a second time point and to provide the positions and time points to the server, the medical device being configured to determine, using the operations sensor, a time point for when the medical device has been in use (third time point), and configured to, using its cellular radio transceiver, establishing a data connection to the server and transferring the third time point to the server, the server being configured to receive at least the first, second and third time points and to select, among at least the first time point and the second time point, the time point that is closest to the third time point and to use the position of the selected time point to retrieve position specific data selected from the group consisting of a weather or climate parameter, air pressure, humidity, temperature, traffic, air pollution, air particle density, air pollen density, person density and altitude above sea level for the for the time point, and to use the position-specific data to determine whether the medical device should be serviced or replaced, where the client device comprises instructions that causes the client device to determine the position at least at predetermined time intervals or where the cell network provides the position of mobile phone cell network to server at predetermined time intervals.

8. The system of claim 7 where the medical device is configured to establish a data connection to the server and transfer the third time point to the server at least at predetermined time intervals.

9. The system of claim 7 where the medical device is configured to establish a data connection to the server and transfer the third time point to the server automatically after the medical device has been in use.

10. The system of claim 7, where the determination step of the server involves the server applying a decision rule, said decision rule being generated by applying machine learning to a data set, said data set comprising previously collected position-specific data for comparable medical devices, said data set also comprising data about previous failures of the comparable portable medical devices.

11. The system of claim 7, where the portable medical device is a device for injection of a medicament.

* * * * *